US010918588B2

(12) United States Patent
Wang et al.

(10) Patent No.: US 10,918,588 B2
(45) Date of Patent: Feb. 16, 2021

(54) BLOCK COPOLYMERS FOR TOOTH ENAMEL PROTECTION

(71) Applicants: COLGATE-PALMOLIVE COMPANY, New York, NY (US); HOWARD UNIVERSITY, Washington, DC (US)

(72) Inventors: Tongxin Wang, Berwyn Heights, MD (US); Yanda Lei, Greenbelt, MD (US); James W. Mitchell, Durham, NC (US); Lynette Zaidel, Cranford, NJ (US); Jian-hong Qiu, Green Brook, NJ (US); Mahmoud Hassan, Somerset, NJ (US)

(73) Assignees: Colgate-Palmolive Company, New York, NY (US); Howard University, Washington, DC (US)

(*) Notice: Subject to any disclaimer, the term of this patent is extended or adjusted under 35 U.S.C. 154(b) by 0 days.

(21) Appl. No.: 14/441,782

(22) PCT Filed: Nov. 8, 2013

(86) PCT No.: PCT/US2013/069199
§ 371 (c)(1),
(2) Date: May 8, 2015

(87) PCT Pub. No.: WO2014/074854
PCT Pub. Date: May 15, 2014

(65) Prior Publication Data
US 2015/0283061 A1 Oct. 8, 2015

Related U.S. Application Data

(60) Provisional application No. 61/780,199, filed on Mar. 13, 2013, provisional application No. 61/724,736, filed on Nov. 9, 2012.

(51) Int. Cl.
| C08F 293/00 | (2006.01) |
| A61Q 11/02 | (2006.01) |
| A61K 8/90 | (2006.01) |
| A61K 6/00 | (2020.01) |
| A61Q 11/00 | (2006.01) |
| A61K 8/21 | (2006.01) |

(52) U.S. Cl.
CPC .............. *A61K 8/90* (2013.01); *A61K 8/21* (2013.01); *A61Q 11/00* (2013.01); *C08F 293/005* (2013.01)

(58) Field of Classification Search
None
See application file for complete search history.

(56) References Cited

U.S. PATENT DOCUMENTS

| 3,066,112 A | 11/1962 | Bowen et al. |
| 3,274,155 A | 9/1966 | Saunders et al. |
| 5,007,930 A | 4/1991 | Dorman et al. |
| 5,085,861 A | 2/1992 | Gerhart et al. |
| 5,108,755 A | 4/1992 | Daniels et al. |
| 5,626,861 A | 5/1997 | Laurencin et al. |
| 5,766,618 A | 6/1998 | Laurencin et al. |
| 5,866,155 A | 2/1999 | Laurencin et al. |
| 5,977,204 A | 11/1999 | Boyan et al. |
| 6,027,742 A | 2/2000 | Lee et al. |
| 6,287,341 B1 | 9/2001 | Lee et al. |
| 6,331,312 B1 | 12/2001 | Lee et al. |
| 6,376,573 B1 | 4/2002 | White et al. |
| 6,387,414 B1 | 5/2002 | Akashi et al. |
| 6,437,040 B2 | 8/2002 | Anthony et al. |
| 6,649,669 B2 | 11/2003 | Dickens et al. |
| 7,230,039 B2 | 6/2007 | Trieu et al. |
| 7,270,813 B2 | 9/2007 | Shimp et al. |
| 7,670,359 B2 | 3/2010 | Yundt et al. |
| 7,727,539 B2 | 6/2010 | Laurencin et al. |
| 7,731,756 B2 | 6/2010 | Maspero et al. |
| 7,740,794 B1 | 6/2010 | Kumar et al. |
| 7,758,882 B2 | 7/2010 | Roeder et al. |
| 7,879,109 B2 | 2/2011 | Borden et al. |
| 7,959,940 B2 | 6/2011 | Gale et al. |
| 8,283,348 B2 | 10/2012 | Guglielmotti et al. |
| 8,304,087 B2 | 11/2012 | Perrier et al. |
| 2002/0127262 A1 | 9/2002 | Akashi et al. |
| 2003/0082808 A1 | 5/2003 | Guan et al. |
| 2004/0002770 A1 | 1/2004 | King et al. |
| 2004/0012335 A1 | 1/2004 | Shon et al. |
| 2004/0023048 A1 | 2/2004 | Schwartz et al. |
| 2004/0071871 A1 | 4/2004 | Queval et al. |
| 2004/0253290 A1 | 12/2004 | Kim et al. |
| 2005/0100581 A1 | 5/2005 | Laurencin et al. |

(Continued)

FOREIGN PATENT DOCUMENTS

| EP | 1569609 | 9/2005 |
| WO | WO 2002/068550 | 9/2002 |

(Continued)

OTHER PUBLICATIONS

Rager et al., Macromol. Chem. Phys., 1999, 200(7), pp. 1672-1680.*
A. Wiegand et al., "Review on fluoride-releasing restorative materials—fluoride release and uptake characteristics, antibacterial activity and influence on caries formation," Dental Materials, 2007, vol. 23(3), p. 343-362.
A.K. Mascarenhas, "Risk factors for dental fluorosis: A review of the recent literature," Pediatric Dentistry 2000, vol. 22(4), p. 269-277.
A.M.P. Dupraz et al., "Biocompatibility screening of silane treated hydroxyapitite powders, for use as filler in resorbable composites," Journal of Materials Science: Materials in Medicine, Dec. 1996, vol. 7(12), p. 731-738. Retrieved from the internet. <URL: http://springer.com>.

(Continued)

Primary Examiner — Brian Gulledge
(74) Attorney, Agent, or Firm — Hoxie & Associates LLC

(57) ABSTRACT

Described herein are block copolymers having hydrophobic blocks and hydrophilic blocks which are effective in binding to the surface of hard tissue; compositions comprising the same, as well as methods of making and using the same.

13 Claims, 9 Drawing Sheets

(56) References Cited

U.S. PATENT DOCUMENTS

| | | | |
|---|---|---|---|
| 2006/0188712 A1* | 8/2006 | Okada et al. | 428/354 |
| 2006/0194008 A1 | 8/2006 | Schwartz et al. | |
| 2006/0204452 A1 | 9/2006 | Velamakanni et al. | |
| 2006/0264531 A1 | 11/2006 | Zhao et al. | |
| 2007/0299177 A1 | 12/2007 | Serobian et al. | |
| 2008/0065228 A1 | 3/2008 | Kim et al. | |
| 2008/0200638 A1 | 8/2008 | Redepenning et al. | |
| 2008/0226547 A1 | 9/2008 | Larsen et al. | |
| 2009/0048358 A1 | 2/2009 | Kim et al. | |
| 2010/0040668 A1 | 2/2010 | Riman et al. | |
| 2010/0092782 A1* | 4/2010 | Perrier | B27K 3/0292 428/413 |
| 2010/0131064 A1 | 5/2010 | Redepenning et al. | |
| 2010/0160467 A1 | 6/2010 | Lee et al. | |
| 2010/0179243 A1 | 7/2010 | Liu et al. | |
| 2010/0322908 A1 | 12/2010 | Everland et al. | |
| 2011/0008460 A1 | 1/2011 | Riman et al. | |
| 2011/0069112 A1 | 3/2011 | Matsumoto et al. | |
| 2011/0171144 A1 | 7/2011 | Wang et al. | |
| 2011/0196061 A1 | 8/2011 | Ashman et al. | |
| 2012/0003163 A1* | 1/2012 | Mordas | A61K 8/0291 424/55 |
| 2012/0128600 A1 | 5/2012 | Chang et al. | |
| 2013/0078310 A1* | 3/2013 | Sill | A61K 9/1075 424/497 |
| 2014/0134116 A1 | 5/2014 | Wang et al. | |

FOREIGN PATENT DOCUMENTS

| | | | | |
|---|---|---|---|---|
| WO | WO 2004/054529 | | 7/2004 | |
| WO | WO 2006/032896 | | 3/2006 | |
| WO | WO 2011 009228 | * | 1/2011 | C09D 5/02 |
| WO | WO 2011/009228 | | 1/2011 | |
| WO | WO 2012/009555 | | 1/2012 | |
| WO | WO 2012/078980 | | 6/2012 | |

OTHER PUBLICATIONS

B. Schouten et al., "Acute allergic skin reactions and intestinal contractility changes in mice orally sensitized against casein or whey," International Archives of Allergy and Immunology, 2008, vol. 147(2), p. 125-134.
C. Deng et al., "Preparation and mechanical property of poly (epsilon-caprolactone)—matrix composites containing nano-apatite fillers modified by silane coupling agents," Journal of Materials Science: Materials in Medicine, Oct. 1, 2010, vol. 21(12), p. 3059-3064.
C. Deng et al., "Effect of Surface Modification of Nano-Hydroxyapatite Particles on In Vitro Biocompatibility of Poly (epsilon-caprolactone)—Matrix Composite Biomaterials," International Journal of Polymeric Materials and Polymeric Biomaterials, Nov. 2011, vol. 60(12), p. 969-978.
C. Hjortsjo et al., "The Effects of Acidic Fluoride Solutions on Early Enamel Erosion in vivo," Caries Research, 2008, vol. 43, p. 126-131 (Abstract).
Carmen Kunze, et al., "Surface modification of tricalcium phosphate for improvement of the interfacial compatibility with biodegradable polymers," Biomaterials, 2003, vol. 24, p. 967-974. Retrieved from the Internet <URL: www.sciencedirect.com>.
E.C. Reynolds, "Remineralization of enamel subsurface lesions by casein phosphopeptide-stabilized calcium phosphate solutions," Journal of Dental Research, 1997, vol. 76, p. 1587-1595.
G.H. Docena et al., "Identification of casein as the major allergenic and antigenic protein of cow's milk," Allergy, 1996, vol. 51(6), p. 412-416.
Ganss et al., "Efficacy of the stannous ion and a biopolymer in toothpastes on enamel erosion/abrasion" J. of Dentistry, 2012, vol. 40, p. 1036-1043, (Abstract).
J.L. Ferracane, "Current Trends in Dental Composites," Critical Reviews in Oral Biology and Medicine, 1995, vol. 6(4), p. 302-318.

J.P. Santerre, et al., "Relation of Dental Composite Formulations to Their Degradation and the Release of Hydrolyzed Polymeric-Resin-Derived Products," Critical Reviews in Oral Biology and Medicine, 2001, vol. 12(2), p. 136-151.
L. Li et al., "Bio-Inspired Enamel Repair via Glu-Directed Assembly of Apatite Nanoparticles: an Approach to Biomaterials with Optimal Characteristics," Advanced Materials, 2011, vol. 23(40), p. 4695-4701, (Abstract).
L. Li et al., "Repair of enamel by using hydroxyapatite nanoparticles as the building blocks," Journal of Materials Chemistry, 2008, vol. 18, p. 4079-4084.
M. Panich et al. "The effect of casein phosphopeptide-amorphous calcium phosphate and a cola soft drink on in vitro enamel hardness," Journal of American Dental Association, 2009, vol. 140, p. 455-460, (Abstract).
P. Tschoppe et al., "Enamel and dentine remineralization by nano-hydroxyapatite toothpastes," Journal of Dentistry, 2011, vol. 39(6), p. 430-437.
PCT International Search Report and Written Opinion of the International Searching Authority dated Mar. 14, 2014 for International Application PCT/US2013/069199, 8 pages.
R.H. Selwitz et al., "Dental caries," The Lancet, 2007, vol. 369(9555), p. 51-59.
Rager et al., "Micelle formation of poly(acrylic acid)—block-poly(methyl methacrylate) block coplymers in mixtures of water with organic solvents", Macromol. Chem. Phys., 1999, vol. 200(7), p. 1672-1680.
S. Wongkhantee et al., "Effect of acidic food and drinks on surface hardness of enamel, dentine, and tooth-colored filling materials," Journal of Dentistry, 2006, vol. 34, p. 214-220, (Abstract).
S.M. Zhang, et al., "Interfacial fabrication and property of hydroxyapatite/polylactide resorbable bone fixation composites," Current Applied Physics, 2005, vol. 5., p. 516-518. Retrieved from the Internet <URL: www.sciencedirect.com>.
Srinivasan et al., "Comparison of the remineralization potential of CPP-ACP and CPP-ACP with 900 ppm fluoride on eroded human enamel: An in situ study", Archives of Oral Biology, 2010, 57:541-544, (Abstract).
Tongxin Wang, et al., "Synthesis of amphiphilic triblock copolymers with multidentate ligands for surface coating of quantum dots," Presentation No. 0711, Poster Session 2d: Development/ Novel Use of Imaging Probes, Sep. 25, 2009 [online]. Retrieved from the internet <URL: www.wmicmeeting.org/abstracts/data/ papers/0711.html> , 2 pages.
Tongxin Wang, et al., "High Strength Bioresorbable Composites for Bone Fixation and Repair," Howard University Health Sciences, Research Day 2011, Apr. 15, 2011, 2 pages.
Tongxin Wang, et al., "Improve the Strength of PLA/HA Composite Through the Use of Surface Initiated Polymerization and Phosphonic Acid Coupling Agent," Journal of Research of the National Institute of Standards and Technology, 2011, vol. 116(5), p. 785-796.
WHO, "Fluorides and Oral Health: Report of a WHO Expert Committee on Oral Health Status and Fluoride Use," WHO Technical Report Series 846 Geneva, Switzerland, World Health Organization, 1994.
Y. Cai et al., "Role of hydroxyapatite nanoparticle size in bone cell proliferation," Journal of Materials Chemistry, 2007, vol. 17, p. 3780-3787.
European Patent Office Extended European Search Report dated Oct. 12, 2015 for European Patent Application No. 13775678.9, 7 pages.
PCT International Search Report and Written Opinion of the International Searching Authority dated May 20, 2013 for International Application No. PCT/US2013/029839, 18 pages.
PCT International Search Report and Written Opinion of the International Searching Authority dated May 20, 2013 for International Application No. PCT/US2013/029858, 18 pages.
Nielsen et al., "Poly(alkyl methacrylate) Tooth Coatings for Dental Care: Evaluation of the Demineralisation-Protection Benefit Using a Time-Resolved In Vitro Method", Polymers, vol. 3, p. 314-329, (2011).

(56) References Cited

OTHER PUBLICATIONS

Schricker et al., "Synthesis and Morphological Characterization of Block Copolymers for Improved Biomaterials", Ultramicroscopy, vol. 110(6), p. 639-649, (2010).
Suzuki et al., "Synthesis of Soluble Phosphate Polymers by Raft and their in vitro mineralization", Biomacromolecules, vol. 7(11), p. 3178-3187, (2006) (Abstract).
Churchley et al., "Synthesis and characterization of low surface energy fluoropolymers as potential barrier coatings in oral care", Journal of Biomedical Materials Research, p. 994-1005, (2008).
Carbopoly Polymer Products by Lubrizol Corporation, copy from Lubrizol webpage.
Guan et al., "Selection of Oral Microbial Adhesion Antagonists Using Biotinylated *Streptococcus sanguis* and a Human Mixed Oral Microflora", Archives of Oral Biology, vol. 56, p. 129-138, (2001).

\* cited by examiner

BLOCK COPOLYMERS FOR TOOTH ENAMEL PROTECTION

CROSS-REFERENCE TO RELATED APPLICATIONS

This application is a 35 U.S.C. § 371 National Phase Application of International Application No. PCT/US2013/069199, filed on Nov. 8, 2013, which claims the benefit of U.S. Provisional Application Ser. No. 61/724,736 filed on Nov. 9, 2012, and U.S. Provisional Application Ser. No. 61/780,199, filed on Mar. 13, 2013. The disclosures of each of the above applications are incorporated herein by reference in their entireties.

BACKGROUND

There is a need for oral care products offering superior protection against acid dissolution of tooth enamel that surpasses traditional fluoride approaches as awareness of erosion and the impact of dietary habits increases among dental practitioners and their patients. Extrinsic and intrinsic acid are the two most important factors governing demineralization, in which the former is prevalent because of the strikingly increased consumption of soft drinks. A. Wiegand et al., "Review on fluoride-releasing restorative materials-fluoride release and uptake characteristics, antibacterial activity and influence on caries formation," Dental Materials, 2007, 23(3): 343-62. An interesting experiment that used soft drinks to etch tooth enamel indicated that the loss rate of enamel in a soft drink was as high as 3 mm per year. R. H. Selwitz et al., "Dental caries," The Lancet, 2007, 369 (9555): 51-9. For example, Coca Cola could reduce the hardness of enamel by 63% of the original enamel hardness after only 100 seconds of erosion. S. Wongkhantee et al., "Effect of acidic food and drinks on surface hardness of enamel, dentine, and tooth-colored filling materials," Journal of Dentistry, 2006, 34: 214-220. Dietary acids such as citric acid are particularly damaging to tooth enamel because these acids not only have an acid pH, but they also have a calcium chelating capacity which enhances enamel dissolution. Hence, it is important to have new protective agents that are readily applied, are biologically suitable, and can coat tooth enamel and protect enamel from erosion and attack by foods such as dietary acids.

Currently, fluoride compounds are widely used to prevent caries formation and have also been identified as minerals that protect against acid erosion if formulated under the right conditions. A. Wiegand et al., "Review on fluoride-releasing restorative materials-fluoride release and uptake characteristics, antibacterial activity and influence on caries formation," Dental Materials, 2007, 23(3): 343-62. R. H. Selwitz et al., "Dental caries," The Lancet, 2007, 369(9555): 51-9. C. Hjortsjo et al. "The Effects of Acidic Fluoride Solutions on Early Enamel Erosion in vivo", Caries Research, 2008, 43: 126-131. But high loading of fluoride may induce dental fluorosis. WHO, "Fluorides and Oral Health: Report of A WHO Expert Committee On Oral Health Status and Fluoride Use," WHO Technical Report Series 846 Geneva, Switzerland, World Health Organization, 1994. A. K. Mascarenhas, "Risk factors for dental fluorosis: A review of the recent literature," Pediatric Dentistry 2000, 22(4): 269-277. Nonfluoride functional agents have also been highlighted to deliver antierosion benefits. Ganss et al. "Efficacy of the stannous ion and a biopolymer in toothpastes on enamel erosion/abrasion" J. of Dentistry, 2012, 40: 1036-1043. There are many publications that also highlight remineralization processes. Nano hydroxyapatite has been employed for remineralization of tooth enamel. L. Li et al., "Bio-Inspired Enamel Repair via Glu-Directed Assembly of Apatite Nanoparticles: an Approach to Biomaterials with Optimal Characteristics," Advanced Materials, 2011, 23(40): 4695-4701. L. Li et al., "Repair of enamel by using hydroxyapatite nanoparticles as the building blocks," Journal of Materials Chemistry, 2008, 18: 4079-4084. Y. Cai et al., "Role of hydroxyapatite nanoparticle size in bone cell proliferation," Journal of Materials Chemistry, 2007, 17: 3780-3787. P. Tschoppe et al., "Enamel and dentine remineralization by nano-hydroxyapatite toothpastes," Journal of Dentistry, 2011, 39(6): 430-7. But the efficiency of enhancing remineralization is highly dependent on the nanostructure of apatite and varies a lot from case to case.

Casein phosphopeptides-armohous calcium phosphate (CPP-ACP) complexes are known to bind to tooth enamel and provide a way for remineralization of the enamel. Srinivasan et al. "Comparison of the remineralization potential of CPP-ACP and CPP-ACP with 900 ppm fluoride on eroded human enamel: An in situ study", Archives of Oral Biology, 2010, 57: 541-544. E. C. Reynolds. "Remineralization of enamel subsurface lesions by casein phosphopeptide-stabilized calcium phosphate solutions," Journal of Dental Research, 1997, 76: 1587-1595. M. Panich et al. "The effect of casein phosphopeptide-amorphous calcium phosphate and a cola soft drink on in vitro enamel hardness," Journal of American Dental Association, 2009, 140; 455-460." However, CPP and other dairy products may have potential health risk to cause allergic reactions, ranging from minor swelling of the mouth to serious anaphylaxis, which can be potentially life threatening. G. H. Docena et al., "Identification of casein as the major allergenic and antigenic protein of cow's milk," Allergy, 1996, 51(6): 412-416. B. Schouten et al., "Acute allergic skin reactions and intestinal contractility changes in mice orally sensitized against casein or whey," International Archives of Allergy and Immunology, 2008, 147(2): 125-134. In view of the latter problems, alternate materials are needed which will not only provide effective protection of tooth enamel, but also are non-toxic, biologically suitable and provide a readily usable synthesis to provide materials which may be effectively used for enamel protection.

SUMMARY

Block amphiphilic copolymers having hydrophobic blocks and hydrophilic phosphonated or phosphorylated or carboxylated blocks have been developed where the copolymers are effective to bind to hard tissue which includes hydroxyapatite (HA), enamel and other calcium phosphate phases. These copolymers bind to and protect the hard tissue from acid erosion. The hydrophilic phosphonated or phosphorylated or carboxylated blocks are effective to bind to the hard tissue and the hydrophobic blocks and are effective to protect the hard tissue from loss of calcium by at least 5 percent after exposure of the hydroxyapatite to the polymers for 0.1-10 minutes and subsequent exposure of the polymer coated hydroxyapatite to a 0.3-1% citric acid solution, such as for 15 minutes at 37° C. as compared to hydroxyapatite that is not bound to the block copolymers. It should be noted that other temperatures and time periods may also be used to illustrate the effect of the composition. In some embodiments, the tooth enamel is exposed to citric acid solution before and/or after applying the block copolymer. In some embodiments, hydrophilic phosphonated or phosphorylated or carboxylated block copolymers are effective to protect the hard tissue from loss of calcium by at least 10 percent. In some embodiments, hydrophilic phosphonated or phosphorylated or carboxylated block copolymers are effective to protect the hard tissue from loss of calcium by at least 15 percent. In some embodiments, hydrophilic phosphonated or phosphorylated or carboxylated block copolymers are effective to protect the hard tissue from loss of calcium by at least 20 percent. In some embodiments, hydrophilic phosphonated or phosphorylated or carboxylated block copolymers are effective to protect the hard tissue from loss of calcium by at least 25 percent. In some embodiments, hydrophilic phosphonated or phosphorylated or carboxylated block copolymers are effective to protect the hard tissue from loss of calcium by about 30 percent. In some embodiments, hydrophilic phosphonated or phosphorylated or carboxylated block copolymers are effective to protect the hard tissue from loss of calcium by at least 30 percent.

In one form, the block copolymers have a molecular weight (Mn) in a range of from about 1,000 to 1,000,000. According to one form, the block copolymers have a molecular weight in a range of 1,000 to 10,000. The hydrophilic blocks may include blocks with pending functional groups such as phosphonic, phosphoryl, carboxyl, sulfonic, amino, hydroxyl groups, or other hydrophilic groups. In an important aspect, the phosphonated or phosphorylated or carboxylated blocks have a molecular weight in a range of from about 200 to about 1,000,000. According to one form, the hydrophobic blocks have a molecular weight in a range of from about 200 to about 1,000,000. The phosphonated or phosphorylated or carboxylated blocks generally comprise from about 10 to about 90 weight percent of the copolymers and the hydrophobic blocks comprise from about 10 to about 90 weight percent of the block copolymers. In any event, the block copolymers are dispersible in an aqueous media and effect protection of tooth enamel from acid erosion. The polymers may be polymers having two blocks (bi-block copolymers), three blocks (tri-block polymers) where there are two blocks which may be hydrophobic and one hydrophilic block or two hydrophilic blocks and one hydrophobic block and multi-armed blocks. Arms extend from a common core and the arms may have one or more blocks.

In one aspect, the polymers have molecular weights of from about 1,000 to about 1,000,000 and hydrophobic and hydrophilic blocks having molecular weights of from about 1,000 to about 1,000,000 which provide a good solubility in water in a range of from about 0.001 to about 100 g/l at 25° C.

In another aspect, compositions which are effective for use in connection with dental hygiene, such as toothpaste, mouthwash, strips, and gel containing trays which include the block copolymers described herein, are effective for reconstituting protection of tooth enamel from acid erosion as described herein. Regular applications of the compositions, which include the block copolymers, are effective for providing a protective layer on tooth enamel at a first time of application, and thereafter. Regular use of the compositions, as by brushing teeth or use of mouthwash, gels, or strips provide a way of regularly applying the copolymers for protection against acid erosion of tooth enamel. The compositions can include any of the block copolymers disclosed herein, and an orally acceptable carrier, and optionally fluoride.

In an important aspect the phosphonated or phosphorylated block copolymers have the general formula:

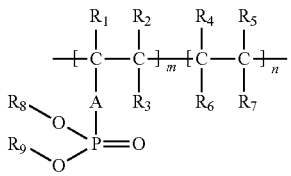

I

In another aspect, the carboxylated copolymers have the general formula:

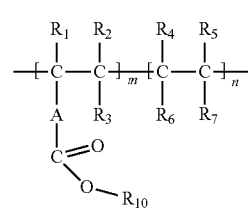

II

Where in the above formulas I and II A is selected from the group consisting of $(CH_2)_p$, $(CH_2CH_2O)_q$, $(phenyl)_x$, $(C(=O)-O)_y$, $(C(=O)-OCH_2CH_2O)_b$, or any combination thereof, where for substituent A p, q=0, 1, 2, 3, 4, 5, 6, 7, 8, 9, 10, 11, 12, 13, 14, 15, 16, 17, 18, 19, or 20; x=0, 1, y=0 or 1, b=0 or 1;

$R_1$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_1$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_2$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_2$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_3$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_3$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_4$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_4$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_5$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_5$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_6$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_6$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_7$ is selected from the group consisting of $H_a$, $(CH_2)_p$, $(CH_2CH_2O)_q$, $(phenyl)_x$, $(C(=O)—O)_y$, $(C(=O)—OH)_c$, $(C(=O)—OCH_3)_d$, $(C(=O)—OC(CH_3)_3)_e$, or any combination thereof, where for $R_7$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_8$ is selected from the group consisting of an alkali metal, an ammonium, protonated alkyl amine, $H_a$, $(CH_2)_p$, $(CH_2CH_2O)_q$, $(phenyl)_x$, $(C(=O)—O)_y$, or any combination thereof, where for $R_8$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_9$ is selected from the group consisting of an alkali metal, an ammonium, protonated alkyl amine, $H_a$, $(CH_2)_p$, $(CH_2CH_2O)_q$, $(phenyl)_x$, $(C(=O)—O)_y$, or any combination thereof, where for $R_9$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_{10}$ is hydrogen, methyl, alkali metal, or ammonium;

m and n are each independently in a range from about 5 to about 3000.

In a preferred embodiment, m is from 5 to 100. In a preferred embodiment, n is from 5 to 400. Preferred block copolymers include poly methyl methacrylate-poly methacryloyloxyethyl phosphate block copolymers, poly methyl methacrylate-poly acrylate acid block copolymers, and poly methyl methacrylate-poly tert-butyl acrylate block copolymers, in particular poly methyl methacrylate-poly methacryloyloxyethyl phosphate block copolymers.

The block copolymers can be synthesized from reversible addition fragmentation chain transfer radical polymerization (RAFT), atomic transfer radical polymerization (ATRP) which often use a catalyst such as a transition metal catalyst and which can effect multi-armed blocks, other chain transfer polymerization, free radical polymerization, ionic polymerization or direct coupling from homopolymers. Also, the block copolymers can be obtained by hydrolyzing their corresponding block copolymers as the precursors which are obtained from the above polymerization techniques.

Initiators include, but are not limited to, benzoyl peroxide, dicumyl peroxide, t-butyl peroxybenzoate, 2,2-azobisisobutyronitrile (AIBN) and other materials that can generate radicals in direct or indirect approaches. The initiators for ATRP can be 2-bromoisobutyryl bromide or others with similar structure.

The general chemical formula for the chain transfer agent (CTA) for RAFT polymerization is shown below:

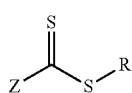

where Z and R can be the same or different substitutes. Typical chain transfer agents include, but are not limited to, cumyldithiobenzoate, 2-cyano-2-yl-dithiobenzoate and 4-cyano-4-[(dodecylsulfanylthiocarbonyl)sulfanyl]pentanoic acid with their structure shown as below.

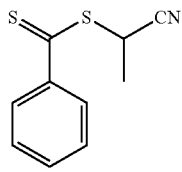

2-cyano-2-yl dithiobenzoate

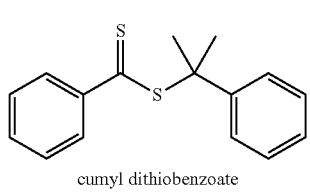

cumyl dithiobenzoate

-continued

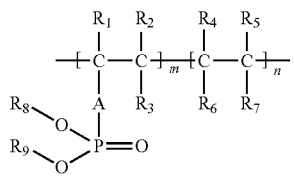

4 cyano 4-[(dodecylsulfanylthiocarbonyl)sulfanyl] pentanoic acid

In an important aspect the copolymers are the reaction product of hydrophobic monomers such as acrylates (alkyl (meth)acrylate, alkyl acrylate), styrene, olefins (ethylene, propylene, butylenes, butadiene), vinyl monomers (vinyl acetate, vinyl ether), fluoro monomers (perflurocarbon, tetrafluoroethylene), acrylonitrile, which will provide the hydrophobic block after polymerization and other hydrophilic monomers to provide the hydrophilic block. The hydrophilic monomers contain polymerizable groups and active phosphate acid, phosphonic acid and related esters, as well as other phosphorous containing monomers, such as alkyl (meth)acryloyloxyethyl phosphate, bis(2-methacryloxyethyl) phosphate, vinyl phosphonic acid and other monomers. The carboxylated hydrophilic monomers include acrylic acid, methyl (meth)acrylic acid, methyl acrylic acid, and other alkyl (meth)acrylic acids. It should be noted that the hydrophilic block can also be indirectly obtained by hydrolyzing the corresponding precursors.

In another aspect, the block copolymers comprise from about 0.001 to about 50 weight percent of a dental hygienic composition such as an ingredient which forms the basis of toothpaste or gel which also includes abrasive particulates such as aluminum hydroxide, calcium carbonate, dicalcium phosphate, and silicas; flavorants, humectants, antibacterial agents, and remineralizers such as fluoride, hydroxyapatite and phosphates such as calcium phosphate. The block copolymers also may be included in aqueous compositions which form the basis of mouthwash which also include fluoride, alcohol, chlorhexidine gluconate, cetylpyridinium chloride, hexetidine, buffers such as benzoic acid, methyl salicylate, benzalkonium chloride, methylparaben, hydrogen peroxide, domiphen bromide and fluoride, enzymes, and calcium. Mouthwash can also include other antibacterials such as, e.g., phenol, thymol, eugenol, eucalyptol or menthol as well as sweeteners such as sorbitol, sucralose, sodium saccharin, and xylitol. In this aspect the copolymers are dispersible in an aqueous media and the block copolymers form from about 0.001 to about 20 weight percent of the aqueous composition which forms the mouthwash.

In yet another aspect, the phosphonated or phosphorylated block copolymers are formed in a two-step reversible addition-fragmentation transfer (RAFT) polymerization or a one pot RAFT polymerization reaction. Illustrative of the two step RAFT reaction is shown below.

Monomer-1 (hydrophobic monomer)+Chain Transfer Agent (CTA)+Free Radical Initiator→Poly(monomer-1)-CTA then Poly(monomer-1)-CTA+Monomer-2 (phosphorous monomer)+Free Radical Initiator→

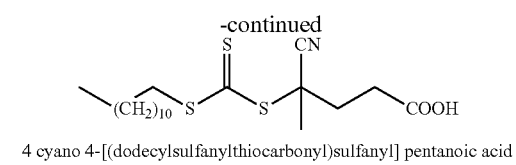

In another aspect, the carboxylated block copolymers are also formed in a two-step RAFT polymerization or a one pot RAFT polymerization reaction. Illustrative of the two step RAFT reaction is shown below.

Monomer-1 (hydrophobic monomer)+CTA+Free Radical Initiator→Poly(monomer-1)-CTA then Poly(monomer-1)-CTA+Monomer-2 (carboxylated monomer)+Free Radical Initiator→

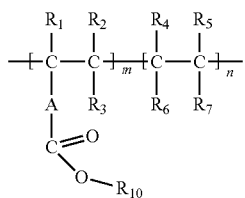

where A is selected from the group consisting of $(CH_2)_p$, $(CH_2CH_2O)_q$, $(phenyl)_x$, $(C(=O)-O)_y$, $(C(=O)-OCH_2CH_2O)_b$, or any combination thereof, where for substituent A p, q=0, 1, 2, 3, 4, 5, 6, 7, 8, 9, 10, 11, 12, 13, 14, 15, 16, 17, 18, 19, or 20; x=0, 1, y=0 or 1, b=0 or 1;

$R_1$ is selected from the group consisting of $H_a$, $(CH_2)$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$ or any combination thereof, where for $R_1$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_2$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_2$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_3$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_3$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_4$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_4$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_5$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_5$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_6$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_6$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_7$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_7$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_8$ is selected from the group consisting of an alkali metal, an ammonium, protonated alkyl amine, $H_a$, $(CH_2)_p$, $(CH_2CH_2O)_q$, $(phenyl)_x$, $(C(=O)-O)_y$, or any combination thereof, where for $R_8$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_9$ is selected from the group consisting of an alkali metal, an ammonium, protonated alkyl amine, $H_a$, $(CH_2)_p$, $(CH_2CH_2O)_q$, $(phenyl)_x$, $(C(=O)-O)_y$, or any combination thereof, where for $R_9$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_{10}$ is hydrogen, methyl, alkali metal, or ammonium; and m and n are each independently in a range from about 5 to about 3000.

In a preferred embodiment, m is from 5 to 100. In a preferred embodiment, n is from 5 to 400.

The block copolymers can be synthesized from reversible addition fragmentation chain transfer radical polymerization (RAFT), atomic transfer radical polymerization (ATRP), other chain transfer polymerization, free radical polymerization, ionic polymerization or direct coupling from homopolymers. Also, the block copolymers can be obtained by hydrolyzing their corresponding block copolymers as the precursors which are obtained from the above polymerization techniques. Additional hydrolysis procedure may be needed if hydrophobic monomers are used as the precursors for hydrophilic block.

Initiators include, but are not limited to, benzoyl peroxide, dicumyl peroxide, t-butyl peroxybenzoate, 2,2-azobisisobutyronitrile (AIBN) and other materials that can generate radicals in direct or indirect approaches. The initiators for ATRP can be 2-bromoisobutyryl bromide or others with similar structure.

The general chemical formula for the chain transfer agent for RAFT is shown below:

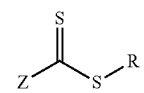

where Z and R can be the same or different substitutes.

In the "one pot" method, the reaction for phosphonated or phosphorylated block copolymer proceeds as follows as part of a single step with the phosphorous acid being added to the reaction mixture having the hydrophobic block:

Monomer-1 (hydrophobic monomer)+Chain Transfer Agent+Free Radical Initiator→Poly(monomer-1)-CTA+Monomer-2 (phosphorous monomer)→

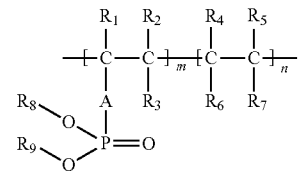

or, in another aspect, the reaction for carboxylated block copolymer proceeds as follows as part of a single step with the carboxylated monomer being added to the reaction mixture having the hydrophobic block:

Monomer-1 (hydrophobic monomer)+Chain Transfer Agent+Free Radical Initiator→Poly(monomer-1)-CTA+Monomer-2 (phosphorous monomer)→

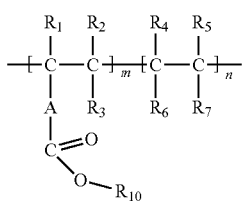

where A is selected from the group consisting of $(CH_2)_p$, $(CH_2CH_2O)_q$, $(phenyl)_x$, $(C(=O)-O)_y$, $(C(=O)-OCH_2CH_2O)_b$, or any combination thereof, where for substituent A p, q=0, 1, 2, 3, 4, 5, 6, 7, 8, 9, 10, 11, 12, 13, 14, 15, 16, 17, 18, 19, or 20; x=0, 1, y=0 or 1, b=0 or 1;

$R_1$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$ or any combination thereof, where for $R_1$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_2$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_2$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_3$ is selected from the group consisting of $H_a$, $(CH_2)P$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_3$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_4$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_4$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_5$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)$ a, $(C(=O)-OC(CH_3)_3)_e$, or any combination thereof, where for $R_5$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_6$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_6$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_7$ is selected from the group consisting of $H_a$, $(CH_2)_p$, $(CH_2CH_2O)_q$, $(phenyl)_x$, $(C(=O)-O)_y$, $(C(=O)-OH)_c$, $(C(=O)-OCH_3)_d$, $(C(=O)-OC(CH_3)_3)_e$, or any combination thereof, where for $R_7$ p, q=0, 1, 2, 3, 4, 5, 6, 7, 8, 9, 10, 11, 12, 13, 14, 15, 16, 17, 18, 19, or 20; x=0, 1, y=0, 1, a=0, 1, c=0, 1, d=0, 1, e=0, 1;

$R_8$ is selected from the group consisting of an alkali metal, an ammonium, protonated alkyl amine, $H_a$, $(CH_2)_p$, $(CH_2CH_2O)_q$, $(phenyl)_x$, $(C(=O)-O)_y$, or any combination thereof, where for $R_8$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_9$ is selected from the group consisting of an alkali metal, an ammonium, protonated alkyl amine, $H_a$, $(CH_2)_p$, $(CH_2CH_2O)_q$, $(phenyl)_x$, $(C(=O)-O)_y$, or any combination thereof, where for $R_9$ p, q=0, 1, 2, 3, 4, 5, 6, 7, 8, 9, 10, 11, 12, 13, 14, 15, 16, 17, 18, 19, or 20; x=0, 1, y=0, 1, a=0, 1;

$R_{10}$ can be hydrogen, methyl, an alkali metal, or an ammonium; and m and n are each independently in a range from about 5 to about 3000.

In a preferred embodiment, m is from 5 to 100. In a preferred embodiment, n is from 5 to 400. The block copolymers can be synthesized from reversible addition fragmentation chain transfer radical polymerization (RAFT), atomic transfer radical polymerization (ATRP), other chain transfer polymerization, free radical polymerization, ionic polymerization or direct coupling from homopolymers. Also, the block copolymers can be obtained by hydrolyzing their corresponding block copolymers as the precursors which are obtained from the above polymerization techniques. Additional hydrolysis procedure may be needed if hydrophobic monomers are used as the precursors for hydrophilic block.

Initiators include, but are not limited to, benzoyl peroxide, dicumyl peroxide, t-butyl peroxybenzoate, 2,2-azobisisobutyronitrile (AIBN) and other materials that can generate radicals in direct or indirect approaches. The initiators for ATRP can be 2-bromoisobutyryl bromide or others with similar structure.

The general chemical formula for the chain transfer agent for RAFT is shown below:

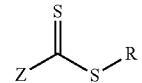

where Z and R can be the same or different substitutes.

In the third aspect, the amphiphilic copolymers are prepared by using a free radical polymerization without RAFT chain transfer agent or by using an atom transfer radical polymerization (ATRP) either from 'one-pot' polymerization or 'two step' polymerization as that for RAFT.

The water solubility and/or dispersibility of the block copolymers may be controlled by the molecular weight of the hydrophilic portion of the copolymer and the ratios of the two blocks. This is done for example by having a feeding ratio and polymerization time of the phosphorous monomer such that a dispersibility or solubility of the block copolymer is from about 0.001 g/L to 100 g/L in water at 25° C.

In embodiments of the block co-polymers, the compositions and/or the methods of the invention, the block co-polymer has Formula 1 or Formula 2 and n is from 5 to 320 and m is from 5 to 320.

In embodiments of the block co-polymers, the compositions and/or the methods of the invention, the block co-polymer is $P(MMA)_{77}$-b-$P(AA)_{23}$, $P(MMA)_{73}$-b-$P(AA)_{28}$, $P(MMA)_{67}$-b-$P(AA)_{64}$, $P(MMA)_{69}$-b-$P(AA)_{198}$, $P(MMA)_{67}$-b-$P(AA)_{318}$, $P(MMA)_{19}$-b-$P(MOEP)_{14}$, $P(MMA)_{19}$-b-$P(MOEP)_9$, $P(MMA)_{17}$-b-$P(AA)_{35}$, $P(MMA)_{17}$-b-$P(MOEP)_{12}$, $P(MMA)_{18}$-b-$P(AA)_{29}$ or $P(MMA)_{19}$-b-$P(MOEP)_9$.

In an embodiment, the term "about" as used herein in regard to a number in a numerical range, for example a positive integer, includes, as a specific embodiment, that specific integer. For example, in an embodiment, "about 5" includes the embodiment of 5.

All combinations of the various elements described herein are within the scope of the invention unless otherwise indicated herein or otherwise clearly contradicted by context.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 2a, 2c and 2e relate to aqueous compositions where the polymers are solubilized at 1 g/L. FIGS. 2b, 2d and 2f relate to aqueous compositions where the polymers are solubilized at 0.2 g/L. The pH of the treatment solution is 3.1 in FIG. 2a, 3.7 in FIG. 2b, 4.2 in FIGS. 2c and 2d and 7.0 in FIGS. 2e and 2f. The insert in FIG. 2a is a FTIR spectrum of a phosphate copolymer.

FIGS. 3-1 to 3-7: FIGS. 3-1 through 3-3 indicate the UV spectra of a phosphate block copolymer before and after binding with HA powder at different conditions. 3-1: UV spectra of P(MMA)$_{19}$-b-P(MOEP)$_9$ with known concentrations. 3-2: UV spectra of P(MMA)$_{19}$-b-P(MOEP)$_9$ after binding with HA powder at pH=4. 3-3: UV spectra of P(MMA)$_{19}$-b-P(MOEP)$_9$ after binding with HA powder at pH=7. FIG. 3-4 through FIG. 3-6 illustrate the UV spectra of carboxylic block copolymers before and after binding with HA at different conditions. 3-4: UV spectra of P(MMA)$_{17}$-b-P(AA)$_{35}$ with standard concentrations. 3-5: UV spectra of P(MMA)$_{17}$-b-P(AA)$_{35}$ after binding with HA powder at pH=4. 3-6: UV spectra of P(MMA)$_{17}$-b-P(AA)$_{35}$ after binding with HA powder at pH=7. FIG. 3-7 shows dependence of phosphorylated block copolymer and carboxylated adsorption on concentration and pH. Lower pH indicates more polymer adsorbed to HA, while the phosphorylated polymer can be adsorbed onto HA more than the carboxylated polymer.

FIGS. 4-1 & 4-2: Show the enamel surface morphology after exposing to acid. 4-1: SEM images of untreated enamel surface before (a) and after (b) acid erosion. 4-2: is the enamel surface morphology which was treated by phosphate block copolymer and then exposed to acid erosion—SEM images of P(MMA)$_{19}$-b-P(MOEP)$_9$ treated-enamel surface before and after acid erosion.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as a terminus of the range and is encompassed by the invention. In addition, all references, patents, patent application publications and books cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES AND TESTS

Figure 1:
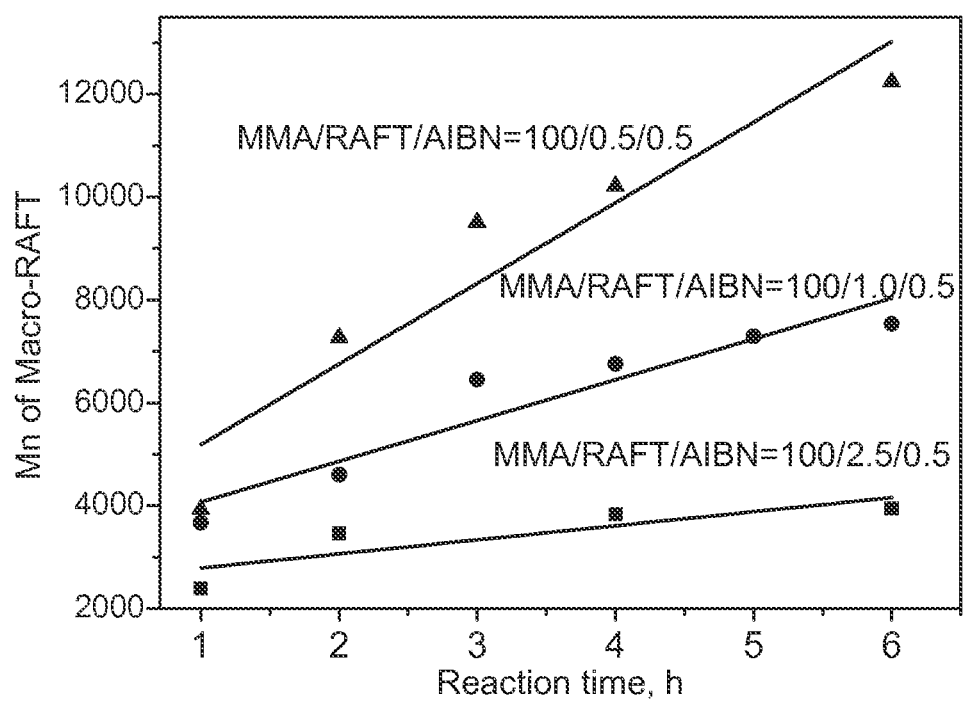
FIG. 1: Controlled synthesis of hydrophobic block via RAFT method by using different monomer/CTA/initiator ratios. MMA stands for methyl methacrylate, CTA stands for chain transfer agent, AIBN stands for azoisobutyronitrile, and MOEP stands for methacryloyloxyethyl phosphate.

1. Controlled synthesis of hydrophobic blocks
2. Block copolymer synthesis
3. Polymer/enamel binding
4, Quantitative analysis of polymer/HA binding
5. Anti erosion test by phosphate block copolymer
6. Anti erosion test by phosphate block copolymer in presence of fluoride
7. SEM observation on the surface morphology of enamel 1. Controlled Synthesis of Hydrophobic Blocks Typically, 10 mmol MMA, 0.25 mmol RAFT CTA agent (e.g. 4-cyano-4-[(dodecylsulfanylthiocarbonyl)sulfanyl] pentanoic acid) and 0.1 mmol AIBN were dissolved in 10 ml 1,4-dioxane. After purging with Argon for 1 h, the system was heated to 70° C. for a period of time. Gel permeation chromatography (GPC) was used to monitor the average macromolecular weight (Mn) of hydrophobic block. For example, Mn of polymethyl methacrylate (PMMA) can be well controlled using different monomer/CTA/initiator ratios as shown in FIG. 1.

2. Block Copolymer Synthesis

Scheme 1. Synthesis of PMMA-b-PMOEP by RAFT method using a chain transfer agent as described above, with "b" being an abbreviation for "block"

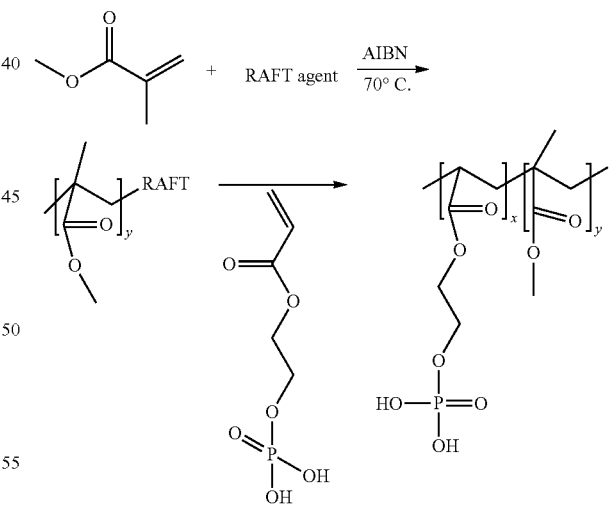

The synthesis of PMMA-b-PMOEP is shown in Scheme 1. Once the targeted Mn of PMMA segment was achieved, certain amounts of methacryloyloxyethyl phosphate (MOEP) in 1,4-dioxane was then injected into the system with syringe and the reaction was further allowed to continue for different reaction times. The composition of PMMA-b-PMOEP could be adjusted by using different feeding ratios and different polymerization times as shown in Table 1.

TABLE 1

Composition of PMMA-b-PMOEP using different polymerization time and feeding ratios

| MMA (mol) | RAFT-chain transfer agent (mol) | AIBN (mol) | MOEP (mol) | Number of MMA in copolymer | Number of MOEP in copolymer |
|---|---|---|---|---|---|
| 100 | 2.5 | 1 | 50 | 17 | 9 |
| 100 | 2.5 | 1 | 50 | 19 | 14 |
| 100 | 2.5 | 1 | 80 | 17 | 14 |
| 100 | 2.5 | 1 | 80 | 20 | 35 |

The synthesis of PMMA-b-PAA by RAFT polymerization is shown in Scheme 2-1. Once the targeted Mn of PMMA segment was achieved, certain amounts of acrylic acid (AA) in 1,4-dioxane was then injected into the system with syringe and the reaction was further allowed to continue for different reaction times. The composition of PMMA-b-PAA could be adjusted by using different feeding ratios and different polymerization times as shown in Table 2. PAA stands for poly acrylate acid.

The synthesis of PMMA-b-PAA can also be prepared by an indirect method shown in Scheme 2-2.

Scheme 2-1. Synthesis of PMMA-b-PAA block copolymers by RAFT method

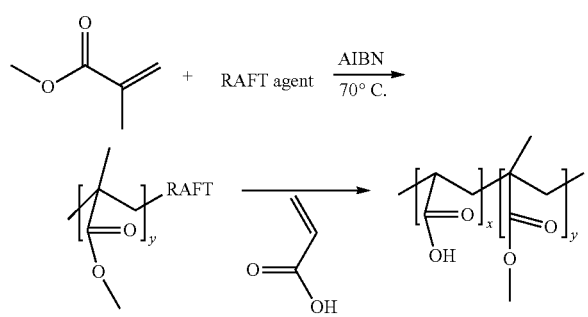

Scheme 2-2. Synthesis of PMMA-b-PAA block copolymers from hydrophobic monomer combined with hydrolysis (tBA stand for tert-butyl acrylate)

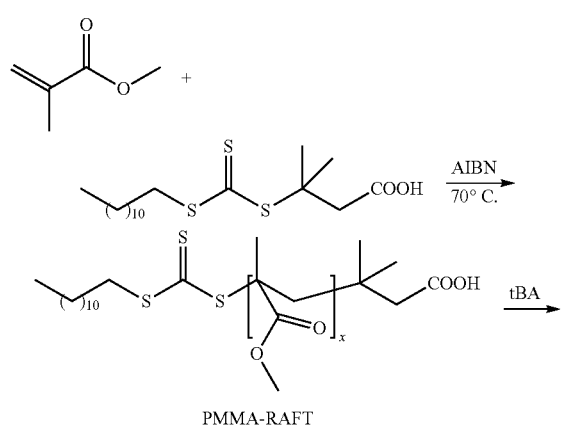

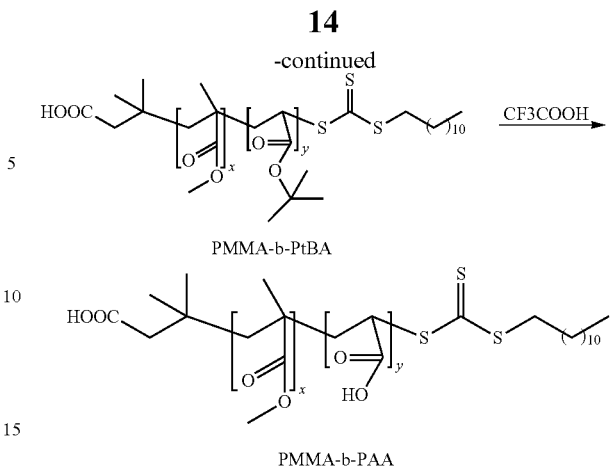

The hydrophobic and hydrophilic block chain lengthen can be adjusted by monomer/CTA/initiator ratio and polymerization time. Different block copolymers with different compositions are shown in Table 2.

TABLE 2

Compositions of carboxylate block copolymers

| Code | Mn | | AA fraction |
|---|---|---|---|
| tBE1 | 9.7k | $PMMA_{77}$-b-$PAA_{23}$ | 0.23 |
| tBE2 | 9.7k | $PMMA_{73}$-b-$PAA_{28}$ | 0.28 |
| tBE3 | 11.7k | $PMMA_{67}$-b-$PAA_{64}$ | 0.49 |
| tBE4 | 21.5k | $PMMA_{69}$-b-$PAA_{198}$ | 0.74 |
| tBE5 | 29.9k | $PMMA_{67}$-b-$PAA_{318}$ | 0.83 |

3. Polymer/Enamel Binding

Figure 2A:
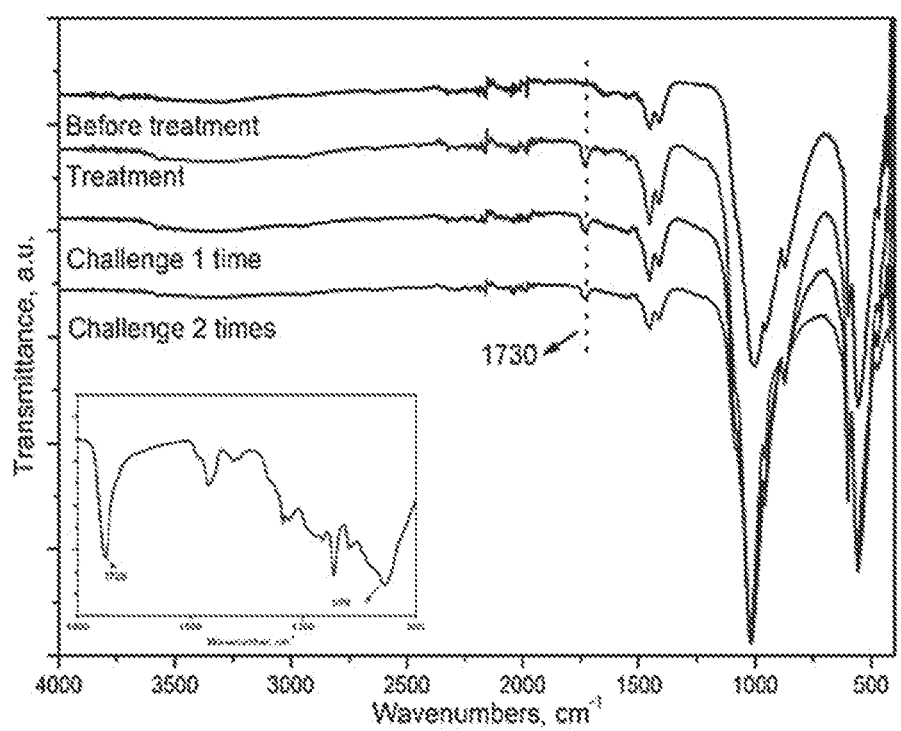
FIGS. 2a-2f: Illustration of Fourier transform Infrared (FTIR) spectra of enamel treated with polymers at different pHs and concentrations.
Figure 2B:
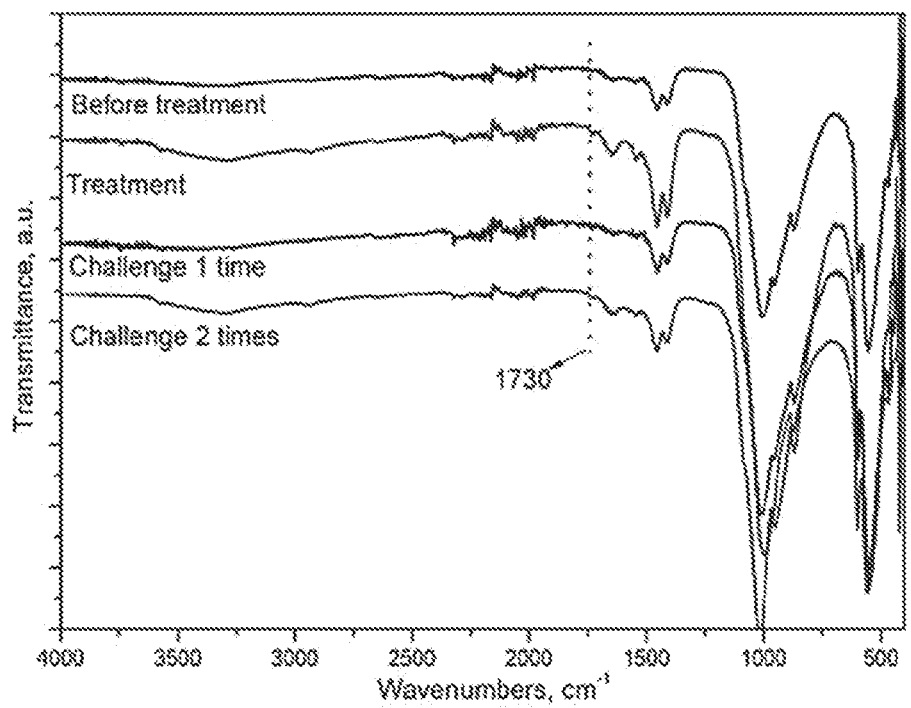
Figure 2C:
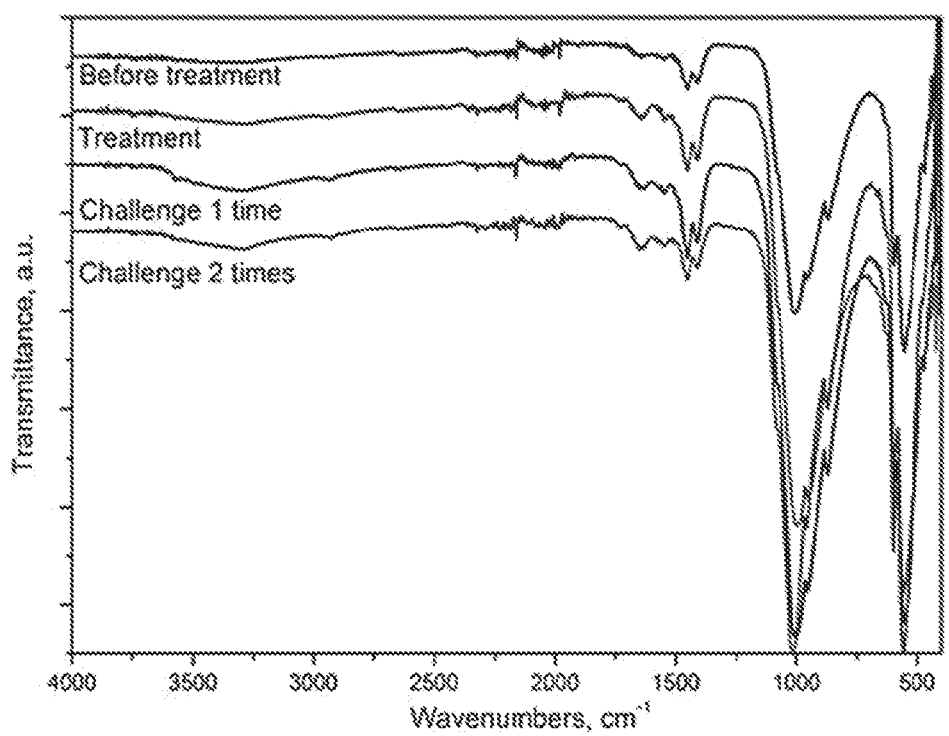
Figure 2D:
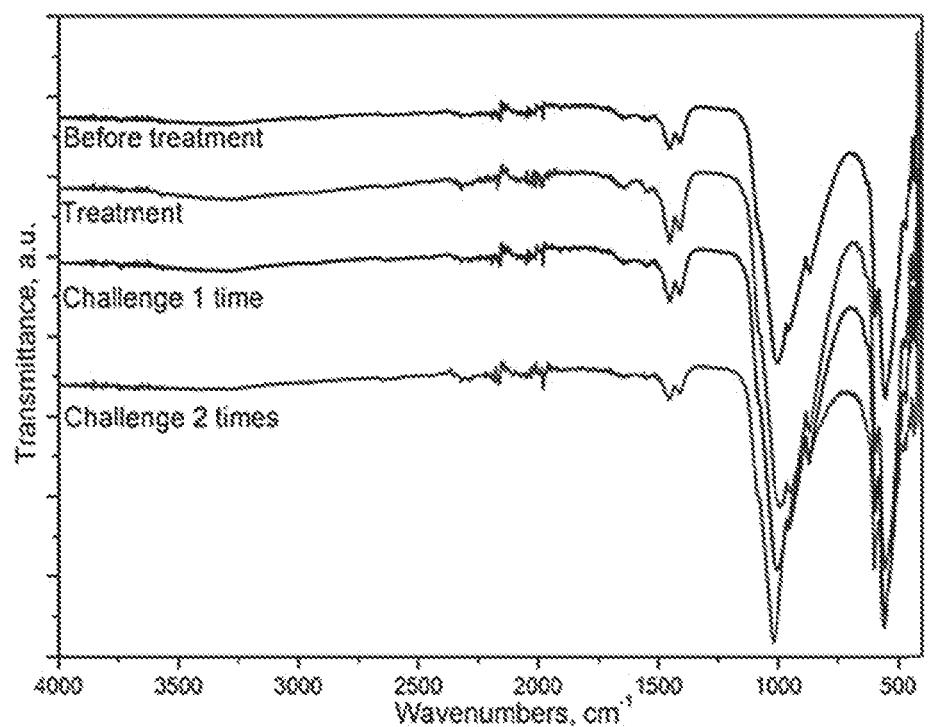
Figure 2E:
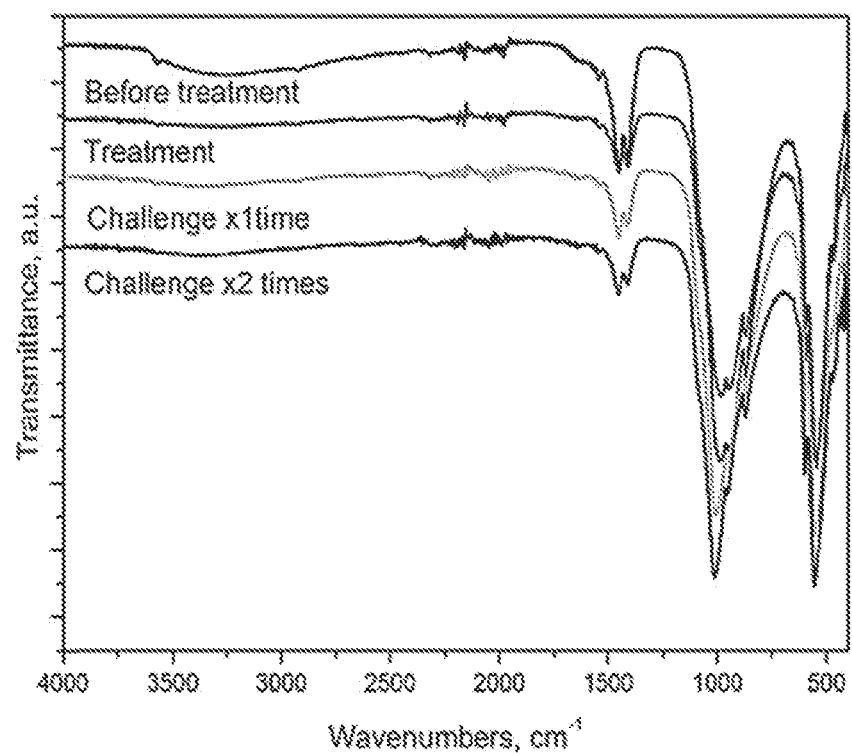
Figure 2F:
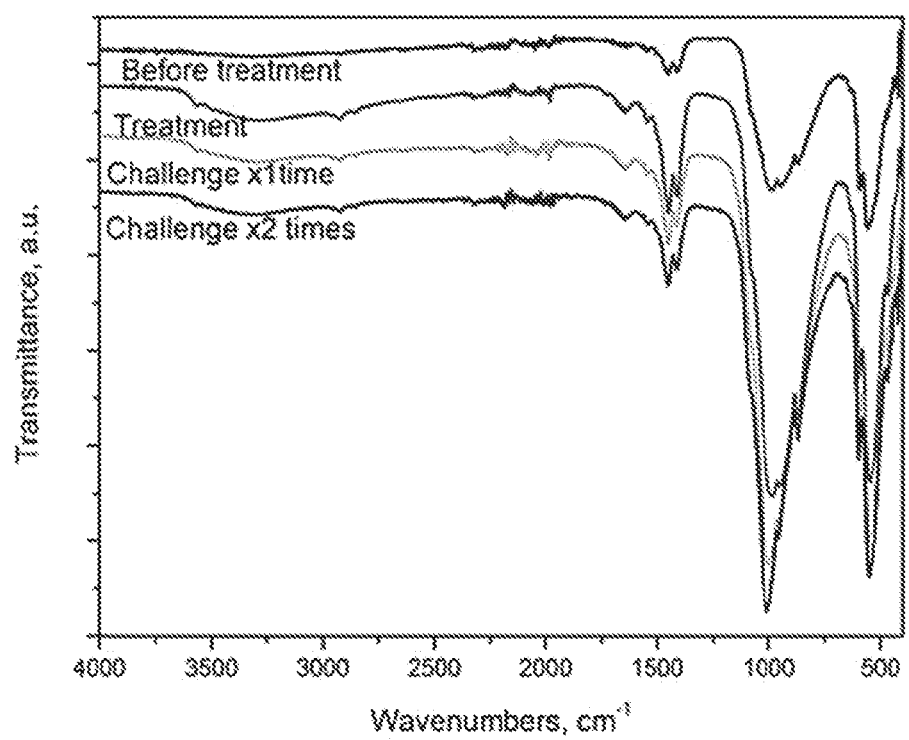
Figures 1, 3:
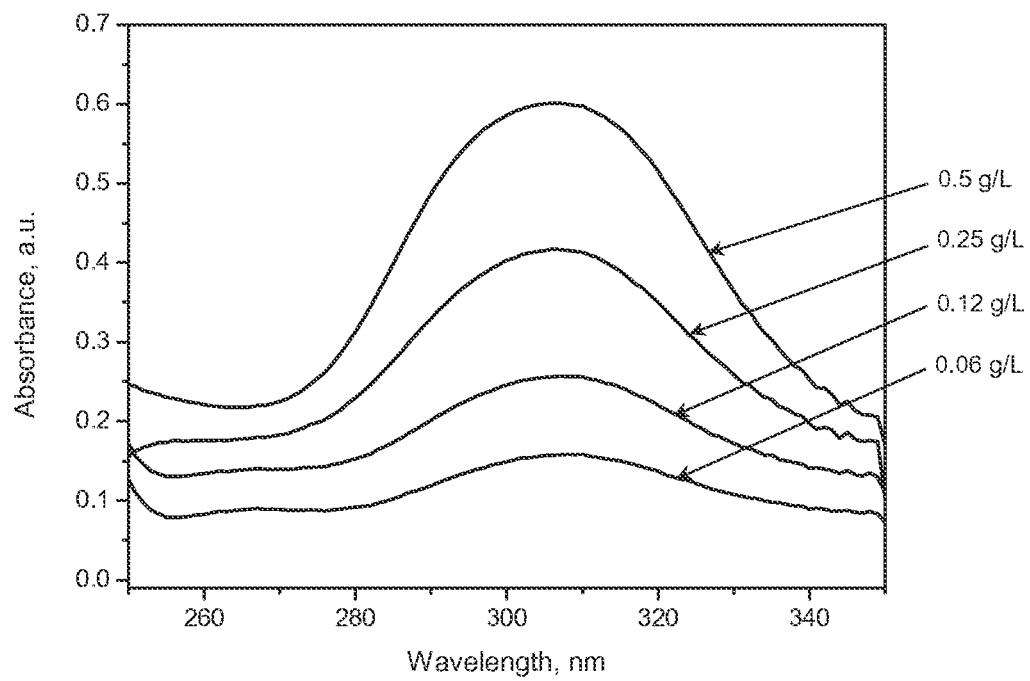
Figures 2, 3:
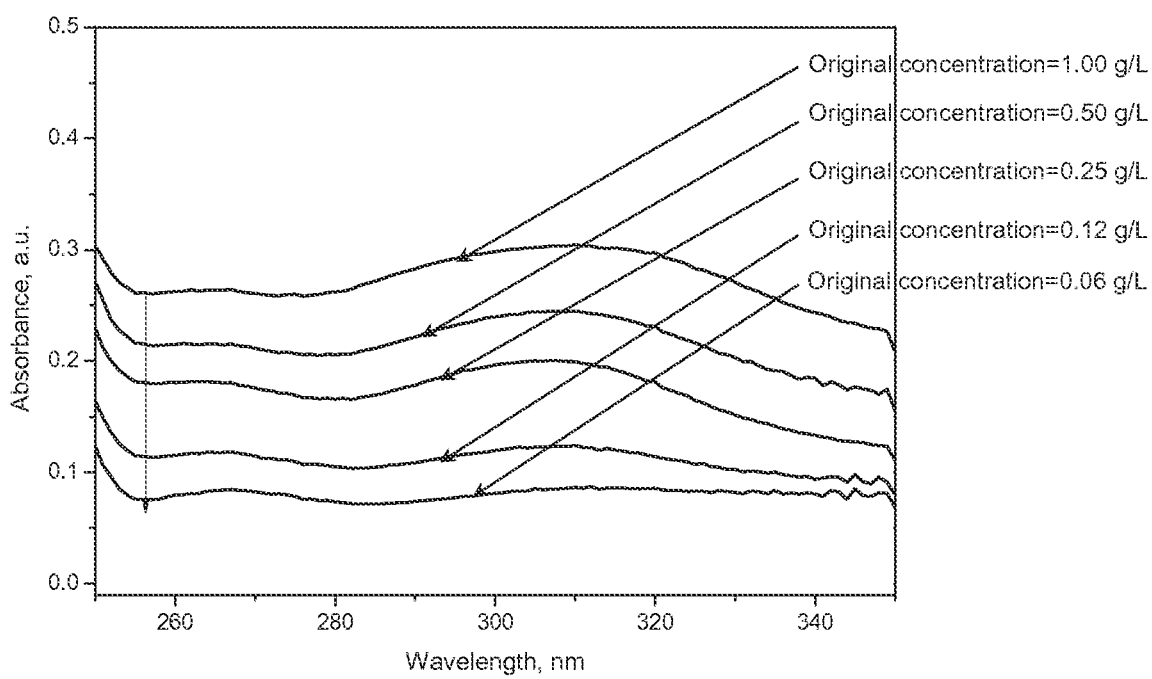
Figure 3:
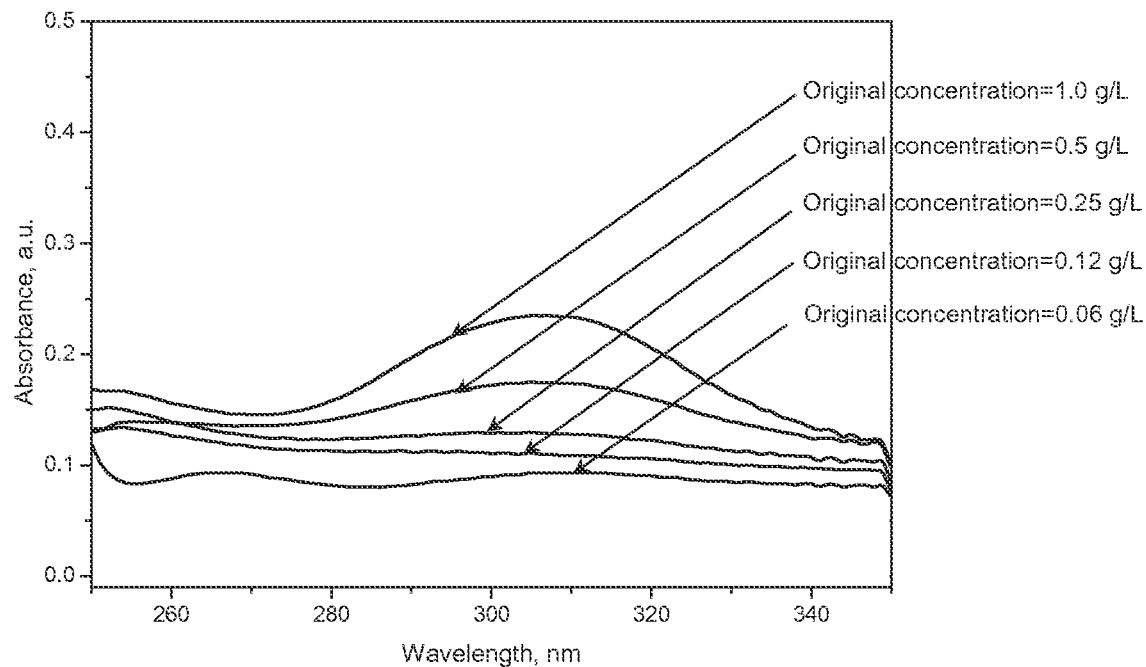

The structure of block copolymer used in this test is $P(MMA)_{19}$-b-$P(MOEP)_{14}$. Before polymer treatment, the surface of bovine enamel was pre-conditioned by immersing the enamel in 1% citric acid solution (pH=3.8) for 5 min. Polymer solution with different concentrations (0.2 and 1.0 g/L) and different pHs (3.1, 4.2 and 7.0) were used to treat the bovine enamel surface for 5 min at 50 rpm. Then the treated surface was washed with phosphate buffer solution (pH=7.0) and acid solution (pH=3.8) for three cycles (5 min/cycle). The treated and etched enamel was characterized by FTIR spectroscopy after air dry. The FTIR spectra are shown in FIG. 2. The peaks at 1452, 1407, and 869 $cm^{-1}$ could be assigned to the existence of carbonated hydroxyapatite on the surface. The peak at 1730 $cm^{-1}$ could be ascribed to the characteristic absorption peak of C=O in block copolymers. Both the effects of polymer concentration and pH on the binding were evaluated. When increasing the polymer concentration from 0.2 to 1.0 g/L, the relative intensity of peak at 1730 $cm^{-1}$ was increased, indicating higher polymer concentration could facilitate the binding efficiency. This could be ascribed to the strong interaction between phosphate groups in the block copolymer and the active site on enamel. Also, from the FIGS. 2a, 2c and 2e, when the pH is increased from 3.1 to 7.0 and the polymer concentration is kept constant as 1.0 g/L, less polymer could be adsorbed onto the enamel surface. The first and second dissociation constants, $pK_{a1}$ and $pK_{a2}$ for phosphoric acid are 2.12 and 7.21, respectively. The phosphate groups of the copolymer are believed to exist in the form of R—$HPO_4^-$ and R—$PO_4^{2-}$, where R stands for the polymer side chains attached to the backbone. The former moiety (R—$HPO_4^-$) will be dominant over the latter one at the pH range (3.1-7.0)

in this test. The phosphate block copolymer with negative charge could bind with the calcium domains on HA surface via electrostatic interaction. A lower pH value of the polymer solutions appears to facilitate the binding.

4. Quantitative Analysis of Polymer/Hydroxyapatite (HA) Binding

The structures of block copolymers used in this test are $P(MMA)_{19}$-b-$P(MOEP)_9$ and $P(MMA)_{17}$-b-$P(AA)_{35}$. Polymer solutions of 5 ml with different concentrations and different pH values were mixed with 100 mg HA powder for 2 h at room temperature. After centrifuging for 10 min at 10000 rpm, the solution was used tested by UV-vis spectroscopy. The absorbance of thiocarbonyl group (C=S) before and after binding were utilized to calculate the adsorbed polymer onto HA powder. The calibration curve was performed by using polymer solution with known concentrations. The UV spectra of phosphorylated or carboxylated block copolymer before and after binding are shown in FIG. 3-1 to FIG. 3-6. The calculated adsorbed polymer bound to HA is shown in FIG. 3-7. It can be seen that when the polymer concentration is gradually increased from 0.06 to 1.0 g/L, more and more polymer could be adsorbed onto the HA surface.

5. Anti Erosion Test of Phosphate Block Copolymer

The structure of block copolymer used in this test is $P(MMA)_{17}$-b-$P(MOEP)_{12}$ and $P(MMA)_{18}$-b-$P(AA)_{29}$. Atomic absorption (AA) spectrometry is one of the most reliable and sensitive methods on evaluating the dental erosion by monitoring the mineral loss. The typical testing procedure used was as follows. First, sintered hydroxyapatite (HA) discs were immersed in 1% citric acid (pH=2.5) for 15 min at room temperature, then soaked in water and sonicated for 30 min. HA discs were fixed on a 6 well plate by using KERR compounds. Note that only the top surface of HA was exposed to the solutions. After air drying, the fixed HA discs were challenged by 1% citric acid (pH=3.8) for 15 min at 37° C. with a shaking speed of 50 rpm. The solution was collected and the calcium concentration was designated as $[Ca]_{ref}$. The HA discs were washed with phosphate buffer solution (PBS, pH=7.0) and then treated with polymer solution (1 g/L) or PBS (as blank) for 2 min. After another washing with PBS, the HA was again challenged with citric acid for another 15 min. The solution was collected and the calcium concentration was measured by AA spectrometry $[Ca]_{treat}$. Because of the heterogeneity among HA samples, the relative calcium level (Ca level), calculated as the following equation (S1), was utilized as an index to assess the protecting efficiency against acid erosion.

$$\text{Ca level} = \frac{[Ca]_{treat}}{[Ca]_{ref}} * 100\% \quad \text{Equation S1}$$

The different polymer treatments on HA surface could influence the calcium level as shown in Table 3. The calcium level after phosphorylated polymer treatments with different polymer treating times was decreased from 91% for blank (non-polymer treated) to 50%, 48%, 34%, 17% for 0.5, 1, 2, or 5 minutes polymer treatment, respectively. The calcium level after carboxylated polymer treatments with different polymer treating time was decreased from 91% for blank (non-polymer treated) to 56%, 60%, 64%, 31% for 0.5, 1, 2, or 5 minutes polymer treatment, respectively. The possible reason is that the adsorbed polymer onto enamel/HA could form a protective layer and prevent the mineral from release.

TABLE 3

Calcium released level (%) following acid erosion challenge

| Treatment | Treating time | | | | |
|---|---|---|---|---|---|
| | 0 | 30 s | 1 min | 2 min | 5 min |
| Blank (PBS buffer) | 90.7 | n/a | n/a | n/a | n/a |
| $P(MMA)_{18}$-b-$P(AA)_{29}$, pH = 4.2 | n/a | 56.4 | 59.6 | 63.9 | 31.2 |
| $P(MMA)_{17}$-b-$P(MOEP)_{12}$, pH = 4.2 | n/a | 50.3 | 48.3 | 34.1 | 16.7 |

The treatment with phosphate monomer and block copolymer on HA surface could influence on the calcium level as shown in Table 4. The calcium level without treatment is 90%. With treatment with phosphate monomer, the calcium level is still around that level, indicating phosphate monomer treatment has a negligible effect on inhibiting mineral loss during acid challenge. Once the HA is treated by phosphate block copolymer, the calcium level is significantly decreased to 43%, meaning that phosphate block copolymer could protect tooth by lowering down the mineral loss during acid challenge. The possible reason is that the adsorbed phosphate block copolymer onto enamel/HA via its phosphate groups and the hydrophobic groups could obstruct the acid attack by forming a protective layer.

TABLE 4

The effect of phosphate monomer and phosphate block copolymer $(P(MMA)_{20}$-b-$P(MOEP)_{35})$ on calcium released level

| Treatment | Concentration, g/L | pH | Calcium Level (%) |
|---|---|---|---|
| Blank (PBS buffer) | n/a | 7.0 | 90.4 ± 13.6 |
| Phosphate monomer | 1.0 | 4.2 | 88.5 ± 12.6 |
| $P(MMA)_{20}$-b-$P(MOEP)_{35}$ | 1.0 | 4.2 | 42.5 ± 7.5 |

The carboxlyate block copolymers' protecting effect is similarly evaluated based on the protocol above and the result is shown in Table 5, where the carboxylic monomer, AA, and its homopolymer, polyacrylic acid (PAA), are also included for comparison. The calcium level was also decreased most for the block co-polymer. The pH value doesn't show a significant influence on the anti erosion behavior of the carboxylate block copolymers.

TABLE 5

The effect of carboxylic monomer (M-AA), acrylic acid homopolymer (AA), and tBE4 (PMMA-b-PAA block copolymer) on calcium released level

| Treatment | Concentration, g/L | pH | Calcium level (%) |
|---|---|---|---|
| Blank (PBS buffer) | n/a | 7.0 | 90.4 ± 13.6 |
| Acrylic acid monomer | 1.0 | 4.2 | 77.6 ± 5.6 |
| PAA | 1.0 | 4.2 | 86.1 ± 14.7 |
| PMMA-b-PAA (tBE4) | 1.0 | 4.2 | 65.3 ± 9.4 |

In order to make a comprehensive comparison, some commercially available copolymers with random structure as well as other carboxylic block copolymers as shown in Table 6. It can be shown that both phosphate and carboxylate block copolymers exhibited a lower value of calcium level released, implying the importance of block structure in protecting tooth from acid challenge. Also, it should be addressed that phosphate block copolymer can more significantly inhibit the mineral loss possibly due to its higher binding strengthen onto HAP surface.

TABLE 6

The effect of different polymers on calcium released level

| Treatment | Concentration, g/L | pH | Calcium level (%) |
|---|---|---|---|
| Blank (PBS buffer) | n/a | 7.0 | 90.4 ± 13.6 |
| P(MMA)$_{20}$-b-P(MOEP)$_{35}$ | 1.0 | 4.2 | 42.5 ± 7.5 |
| PAA | 1.0 | 4.2 | 86.1 ± 14.7 |
| Carbopol | 1.0 | 4.2 | 82.5 ± 12.8 |
| Gantrez | 1.0 | 4.2 | 98.2 ± 4.9 |
| PMMA-b-PAA (tBE4) | 1.0 | 4.2 | 65.3 ± 9.4 |

Another anti erosion test completed for the phosphorylated or carboxylated block copolymers was performed using the pH stat instrument. In this experiment, HAP discs were immersed in 15 ml 0.3% citric acid solution (pH 3.8) for 15 minutes before and after 2-minute treatment. The amount of the 10 mM HCl added over time to keep a pH 3.8 was recorded. The % reduction (anti-erosion efficiency) is calculated as $$\left(1 - \frac{\left(\frac{\text{acid addtion}}{\text{time}}\right)_{\text{after}}}{\left(\frac{\text{acid addtion}}{\text{time}}\right)_{\text{before}}}\right) * 100.$$

The higher reduction indicates better protection on erosion. The corresponding results are shown in Table 7. Similar to the findings obtained for the calcium release experiments, the PMAA homopolymer offered almost no protection (0.65%) while the PMMA-b-PAA block copolymers provided greater protection benefits and the PMMA-b-PMOEP block co-polymer provided the greatest benefits, a 30% reduction in erosion. In addition, increasing the molecular weight of the block co-polymer increases the anti-erosion efficacy

TABLE 7

Anti-erosion efficiency of homo and block co-polymers

| Treatment | Concentration, g/L | Reduction, % |
|---|---|---|
| PAA (MW = 50,000, Polysciences, Inc) | 1.00 | 0.65 |
| (PMMA)69-b-(PAA)198 | 1.00 | 15.16 |
| (PMMA)20-b-P(AA)19 | 1.00 | 10.00 |
| (PMMA)19-b-(PMOEP)9 | 1.00 | 30.37 |

6. Anti Erosion Test of Phosphate Block Copolymer in Presence of Fluoride

Since the fluoride ion is widely used in oral care to protect enamel against acid attack, phosphorylated copolymers can greatly enhance the efficiency of this traditional treatment based on the pH stat assessment. It is clearly shown that the anti-erosion efficiency of the mixture of NaF and polymer is increased by 15-30% compared with the copolymer or NaF alone. This result clearly indicates that it's highly promising to enhance the benefits of fluoride when combining with those claimed block copolymer as oral products. Table 8 shows the anti-erosion protection benefits of the PMMA-b-PMOEP block copolymers (1 g/L) in the presence of 500 ppm F.

TABLE 8

Anti-erosion efficiency of NaF and NaF + PMMA-b-PMOEP

| Treatment | Reduction, % |
|---|---|
| NaF | 30.21 |
| NaF + (PMMA)$_{19}$-b-(PMOEP)$_9$ | 54.29 |
| (PMMA)$_{19}$-b-(PMOEP)$_9$ | 30.37 |

7. Surface Morphology

Figures 3, 4:
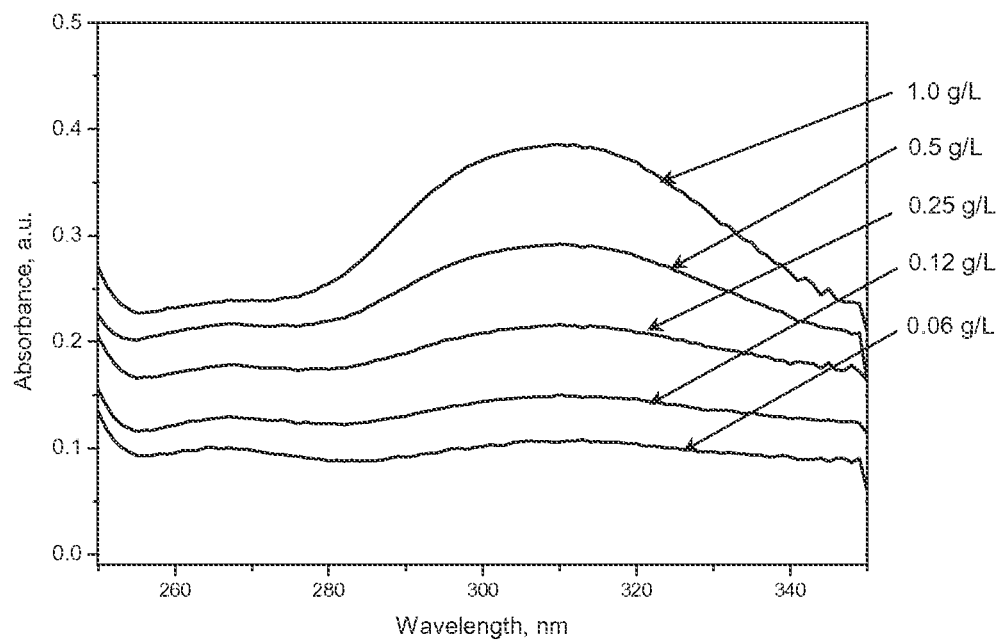
Figures 3, 4, 5:
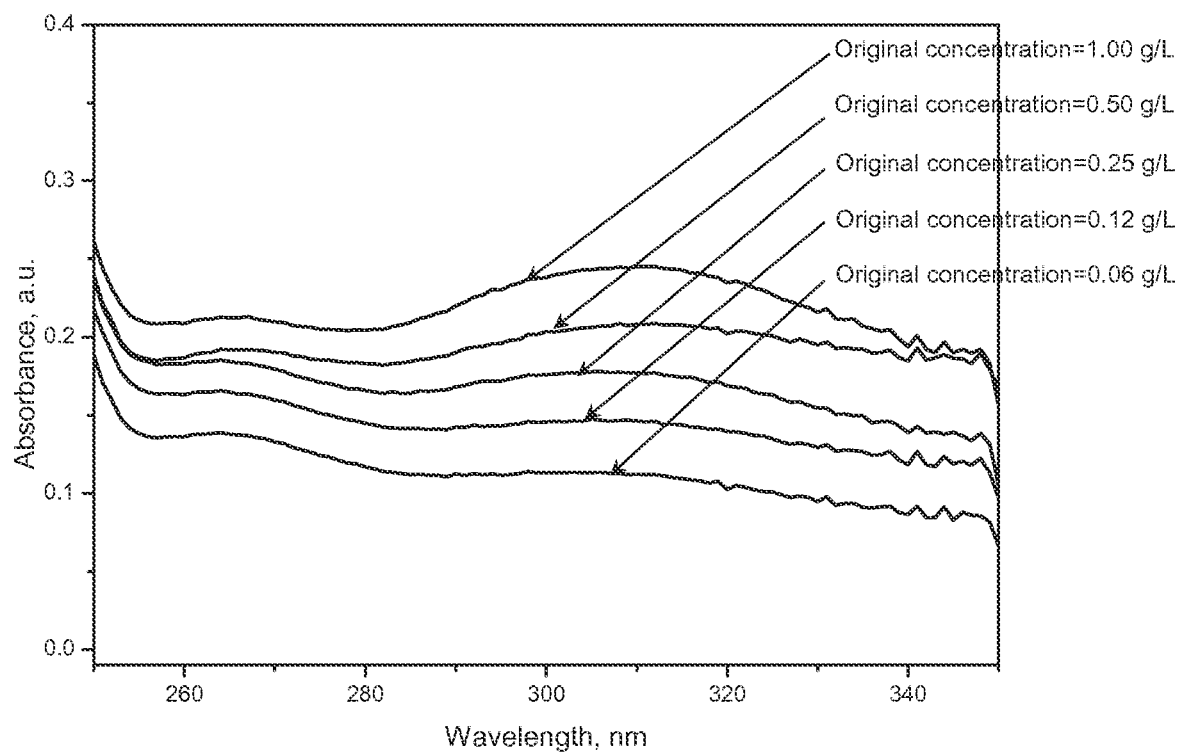
Figures 3, 4, 5, 6:
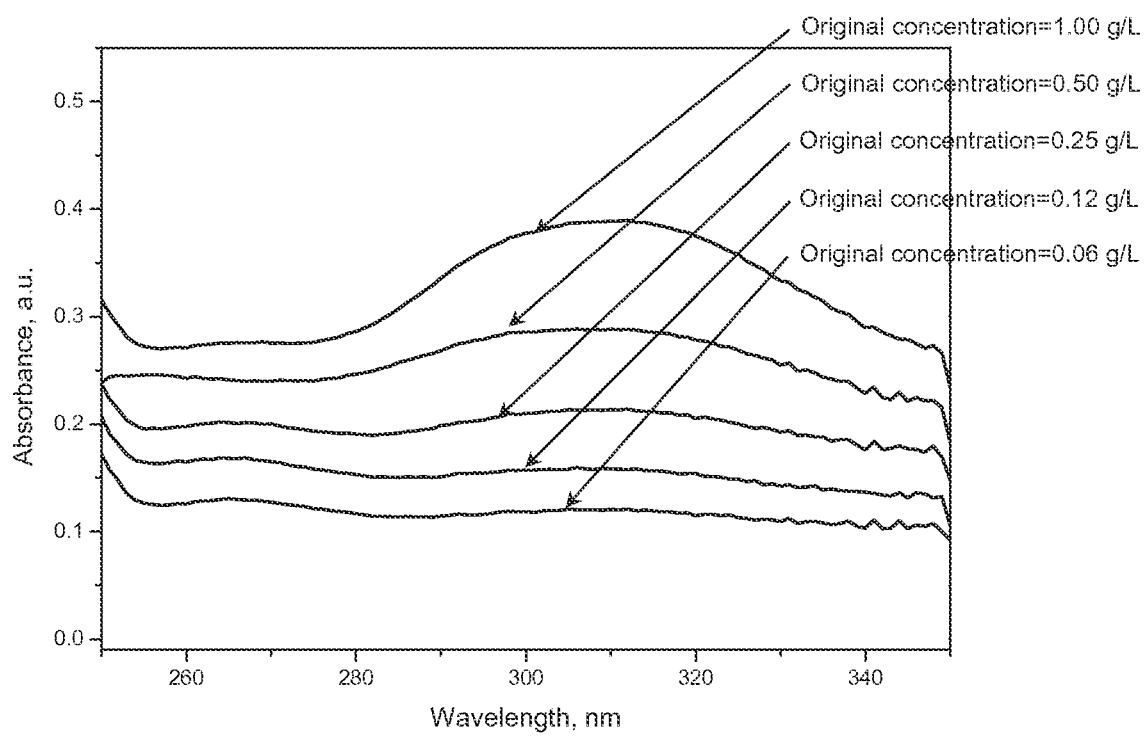
Figures 3, 4, 5, 6, 7:
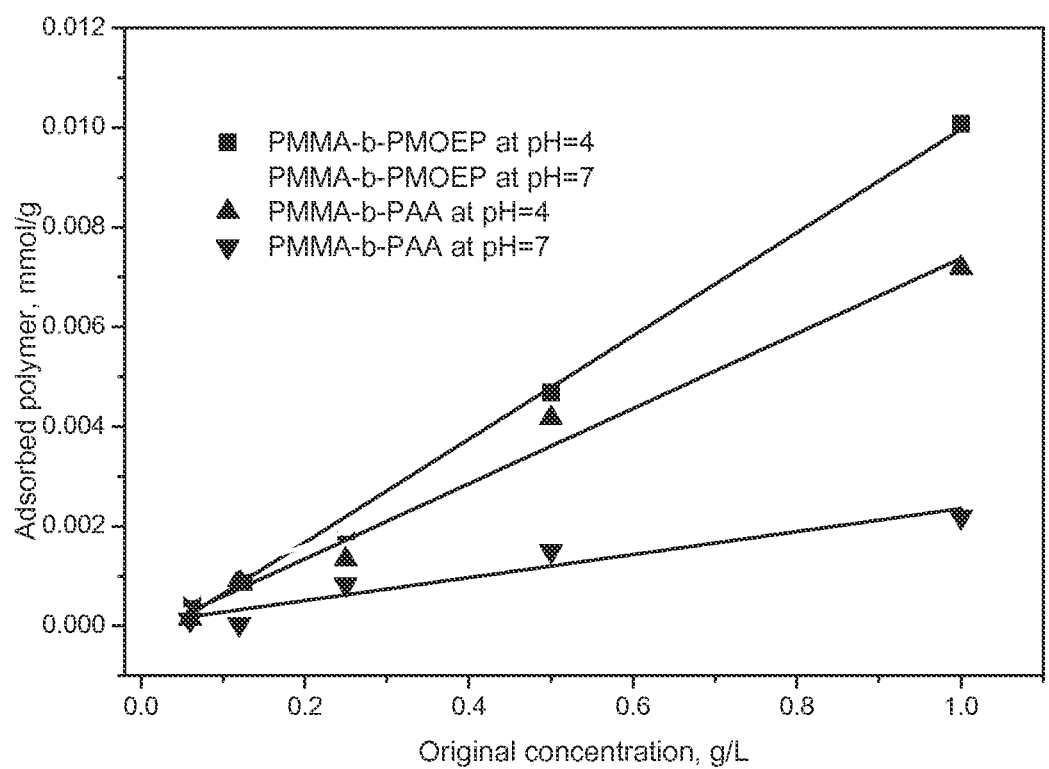
Figures 1, 4:
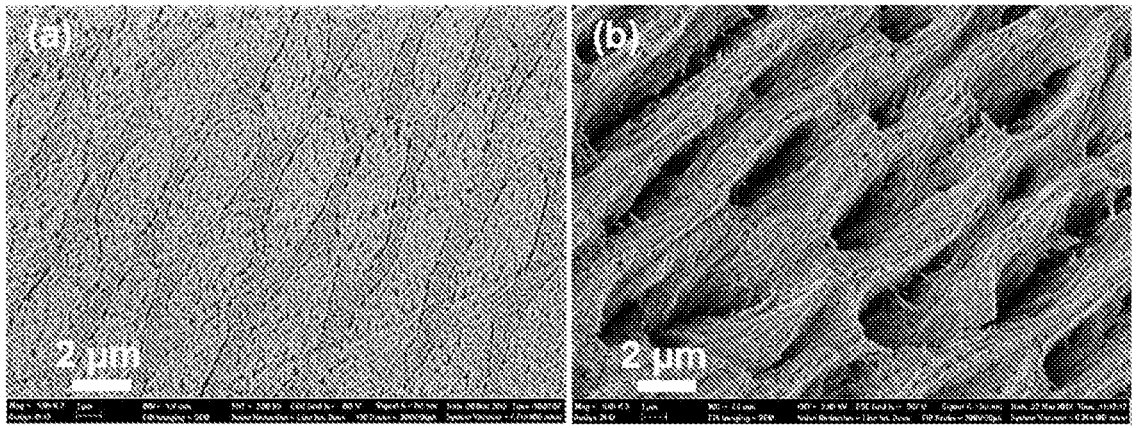
Figures 2, 4:
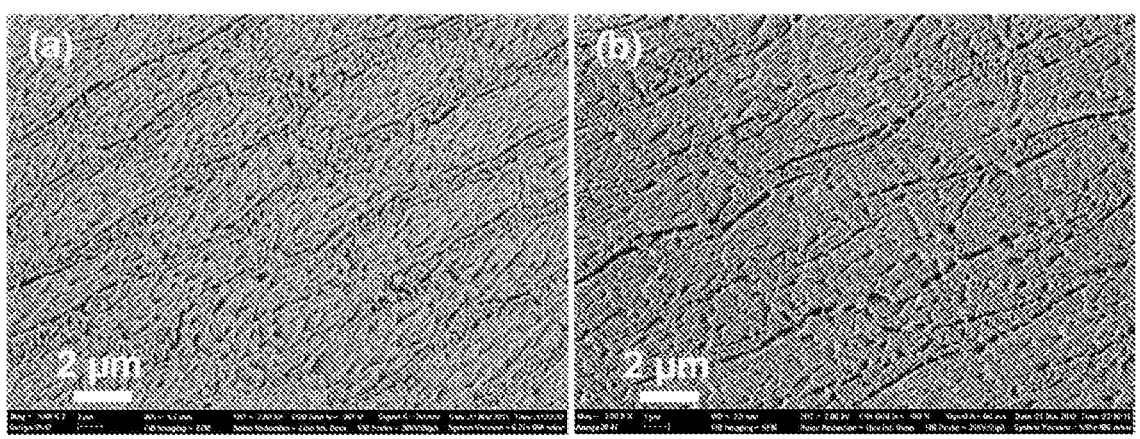

The protective layer that is formed on the enamel surface could prevent the mineral loss as indicated by previous data. This layer could also protect the surface morphology of enamel surface by obstructing the diffusion of external acid. Without any treatment, enamel could be easily etched by acid as shown in FIG. 4. When the surface was treated by phosphate block copolymer first, the surface morphology before and after acid erosion, the tooth surface was largely preserved as shown in FIG. 4-2.

What is claimed is:

1. An oral hygienic composition comprising: an orally acceptable carrier; fluoride, and a block copolymer having at least one hydrophobic block and at least one hydrophilic block in an amount effective to bind hydroxyapatite; and wherein the oral hygienic composition is selected from the group consisting of:
   toothpaste, mouthwash, strips, and gel containing trays; and
   wherein the composition comprises effective amounts of fluoride, the block copolymer, and the carrier to reduce citric acid erosion of hydroxyapaptite by 15-30% as compared to the same composition without fluoride;
   wherein the block copolymer is a poly methyl methacrylate-poly methacryloyloxyethyl phosphate block copolymer or a poly methyl methacrylate-poly acrylate acid block copolymer.

2. The oral hygienic composition of claim 1, wherein the block copolymer is effective to protect the hydroxyapatite from loss of calcium by at least about 10 percent after exposure of the hydroxyapatite to the copolymer and subsequent exposure of the copolymer coated hydroxyapatite to citric acid.

3. The oral hygienic composition of claim 1, wherein the block copolymer has a molecular weight in the range of 1,000 to 1,000,000, individual hydrophilic blocks having a molecular weight in the range of 200 to 1,000,000, and individual hydrophobic blocks having a molecular weight in the range of 200 to 1,000,000.

4. The oral hygienic composition of claim 1, wherein the hydrophilic blocks comprise from 10 to 90 weight percent of the block copolymer and the hydrophobic blocks comprise from 10 to 90 weight percent of the block copolymer.

5. The oral hygienic composition of claim 1, wherein the block has a molecular weight and the polymers have a total molecular weight effective to provide a solubility in water of 0.001 to 100 g/l.

6. The oral hygienic composition of claim 1, wherein the block copolymer has a molecular weight in a range of 1,000 to 1,000,000.

7. The oral hygienic composition of claim 1, wherein the block copolymer has a molecular weight in a range of 1,000 to 10,000.

8. A method for protecting tooth enamel from acid erosion, the method comprising: applying a block copolymer according to claim 1 to tooth enamel, the block copolymer having at least one hydrophobic block and at least one hydrophilic block which are effective to bind to hydroxyapatite.

9. The method of claim 8, wherein the block copolymer is effective to protect the hydroxyapatite from loss of calcium by at least about 10 percent after exposure of the hydroxyapatite to the copolymer and subsequent exposure of the copolymer coated hydroxyapatite to citric acid.

10. The method of claim 8, wherein the block copolymer has a molecular weight in a range of from about 1,000 to have 1,000,000.

11. The method of claim 8, wherein the block copolymer has a molecular weight in the range of from about 1,000 to about 1,000,000, individual hydrophilic blocks having a molecular weight in the range of from about 200 to about 1,000,000, and individual hydrophobic blocks having a molecular weight in the range of from about 200 to about 1,000,000.

12. The method of claim 8, wherein the hydrophilic blocks comprise from about 10 to about 90 weight percent of the block copolymer and the hydrophobic blocks comprise from about 10 to about 90 weight percent of the block copolymer.

13. The method of claim 8, wherein the tooth enamel is exposed to a citric acid solution before and/or after applying the block copolymer.

* * * * *